United States Patent [19]

Meadows

[11] Patent Number: 4,892,188
[45] Date of Patent: Jan. 9, 1990

[54] SANITARY CONDOM CASE

[76] Inventor: Margaret A. Meadows, 1089 Highland Dr., St. Albans, W. Va. 25177

[21] Appl. No.: 279,509

[22] Filed: Dec. 5, 1988

[51] Int. Cl.⁴ ............................................... B65D 85/14
[52] U.S. Cl. ..................................... 206/223; 206/233; 206/69; 206/38
[58] Field of Search ................. 206/233, 236, 237, 69, 206/223, 235, 38

[56] References Cited

U.S. PATENT DOCUMENTS

| 1,221,896 | 4/1917 | Page | 206/237 |
| 1,625,547 | 4/1927 | Kessler | 206/231 X |
| 2,471,963 | 5/1949 | Kaplan | 206/236 X |

FOREIGN PATENT DOCUMENTS

| 119314 | 9/1984 | European Pat. Off. | 206/233 |
| 314166 | 6/1929 | United Kingdom | 206/236 |
| 456240 | 11/1936 | United Kingdom | 206/235 |

Primary Examiner—William Price
Attorney, Agent, or Firm—Leon Gilden

[57] ABSTRACT

A sanitary condom case is presented wherein a pivotally mounted lid is securable to an underlying container including an elongate spring for securement of a plurality of condoms therewithin the container. The lid has formed onto a top surface thereof a dispensing portion for securement of a plurality of pre-mositened cleansing towels with an access opening and a securement strip overlying the access opening wherein the securement strip is provided with a sponge-like vapor barrier laminate for maintaining moisture within the cleansing towels. The securement strip is provided with a hook and loop fastener arrangement about a perimeter thereof for cooperation with companion hook and loop fasteners formed about the lid and access opening. Formed to an interior surface of the lid are a plurality of opposed clips for securement of a polymeric bag for sanitary disposal of the various components.

6 Claims, 1 Drawing Sheet

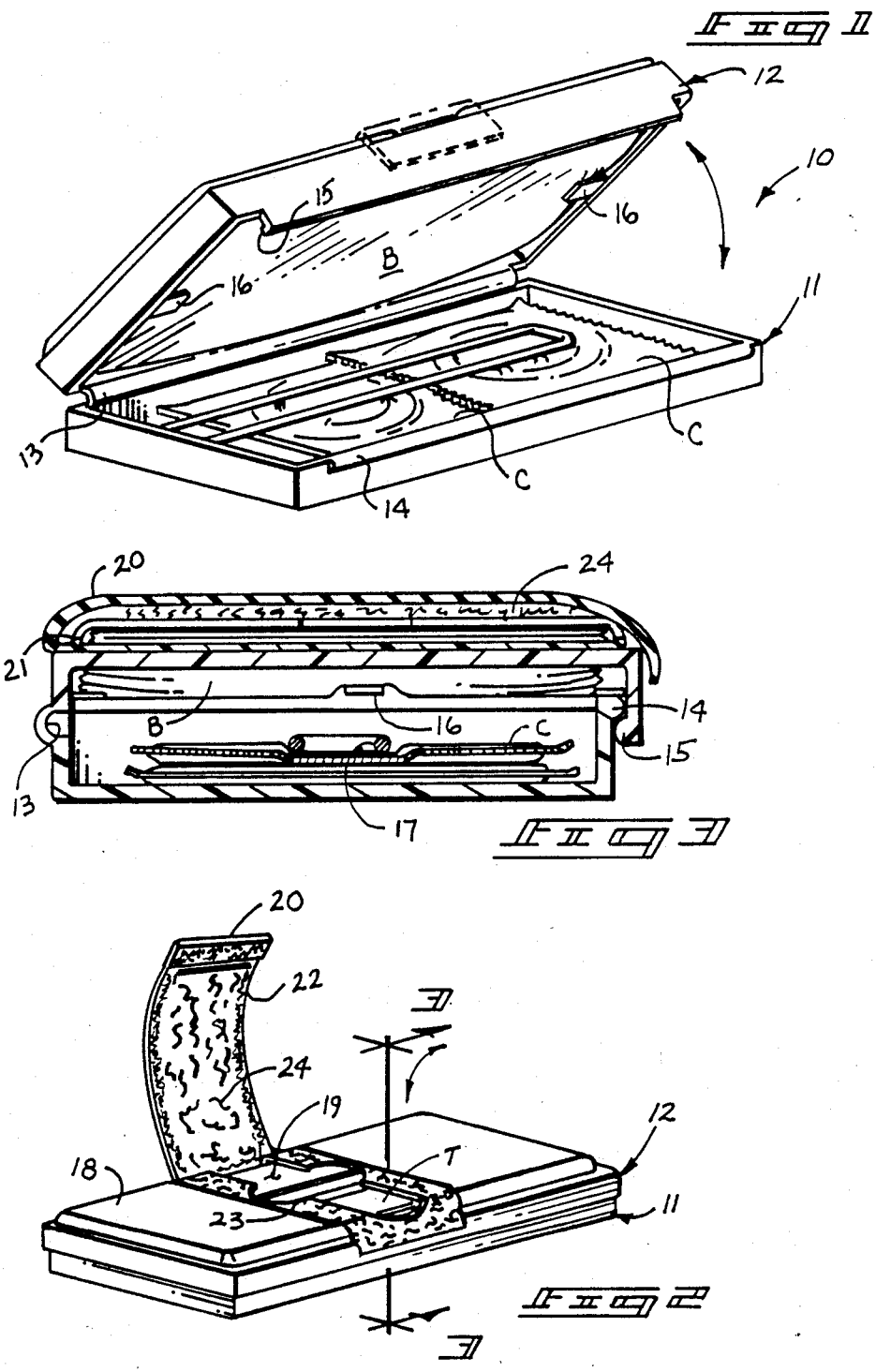

SANITARY CONDOM CASE

BACKGROUND OF THE INVENTION

1. Field of the Invention

The field of invention relates to condom cases, and particularly pertains to a new and improved condom case to provide a convenient storage of various components.

2. Description of the Prior Art

The use of condom cases is well known in the prior art. The condom cases of the prior art, however, have failed to provide a condom container provided with the various components such as condoms, pre-moistened cleansing towels, and a disposable bag for sanitary disposal of the various components. For example, U.S. Pat. No. 4,741,434 to Liebman sets forth a condom case formed as a key chain holder wherein the case is formed of friction members to securably secure plural mirror image portions of the case together. The case of Liebman merely provides for a central compartment for the securement of the condom therewithin.

U.S. Pat. No. 2,008,875 to Peterson sets forth a condom case wherein the container is expressly provided with a plural series of condoms for compact storage within the case.

U.S. Pat. No. 2,332,857 to Karg sets forth a condom container provided with a compartment for the storage of condoms therewithin in a manner similar to the other prior art devices failing to set forth the system of components as provided by the instant invention.

U.S. Pat. No. 4,289,232 to Seibel sets forth a diaphragm case utilizing upper and lower portions provided with an internal container for containment of a contraceptive gel therewithin. The Seibel patent is a further advancement in the prior art by providing a contraceptive securement case utilizing a plurality of components, but fails to set forth the various interrelated components in a compact case, as does the instant invention.

U.S. Pat. No. 706,330 to Menges sets forth an early prior art device wherein a pivoted lid secures a resilient bag therewithin and is of interest relative to the prior devices available.

As such, it may be appreciated that there continues to be a need for a new and improved sanitary condom case wherein the same addresses both the problems of compactness, storage, and provision of various component securement means for containing and providing dispensing of various components associated with sanitary utilization of condoms.

SUMMARY OF THE INVENTION

In view of the foregoing disadvantages inherent in the known types of condom cases now present in the prior art, the present invention provides a sanitary condom case wherein the same provides for the storage and dispensing, when desired, of various components associated with condom utilization. As such, the general purpose of the present invention, which will be described subsequently in greater detail, is to provide a new and improved sanitary condom case which has all the advantages of the prior art condom cases and none of the disadvantages.

To attain this, the present invention sets forth a condom case utilizing an underlying container with a pivotally securable lid thereto wherein the container provides for an elongate resilient clip for securement of a plurality of condoms thereunder. The lid is provided with an overlying dispensing compartment formed with a medially positioned access opening for dispensing of cleansing towels therewithin and further providing for a closure strip formed with perimeter hook and loop fastening structures cooperative with hook and loop fastening structure formed on the lid with a central sponge-like vapor sealing sponge to contain and preserve the cleansing towels. An interior surface of the lid confronting the container is provided with a plurality of spaced clips for securement of a sanitary disposable polymeric bag for the disposing of the cleansing towels and condoms.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved sanitary condom container which has all the advantages of the prior art condom cases and none of the disadvantages.

It is another object of the present invention to provide a new and improved sanitary condom container which may be easily and efficiently manufactured and marketed.

It is a further object of the present invention to provide a new and improved sanitary condom container which is of a durable and reliable construction.

An even further object of the present invention is to provide a new and improved sanitary condom container which is susceptible of a low cost of manufacture with regard to both materials and labor, and which accordingly is then susceptible of low prices of sale to the consuming public, thereby making such sanitary condom container economically available to the buying public.

Still yet another object of the present invention is to provide a new and improved sanitary condom container which provides in the apparatuses and methods of the prior art some of the advantages thereof, while simultaneously overcoming some of the disadvantages normally associated therewith.

Still another object of the present invention is to provide a new and improved sanitary condom container wherein the same securably and compactly maintains condoms and associated paraphernalia in a compact container-like organization.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is an isometric illustration of the instant invention wherein the case is pivoted to an open position.

FIG. 2 is an isometric illustration of the instant invention wherein the case is pivoted to a closed position.

FIG. 3 is an orthographic view taken along the lines 3—3 of FIG. 2 in the direction indicated by the arrows.

DESCRIPTION OF THE PREFERRED EMBODIMENT

With reference now to the drawings, and in particular to FIGS. 1 to 3 thereof, a new and improved sanitary condom case embodying the principles and concepts of the present invention and generally designated by the reference numeral 10 will be described.

More specifically, it will be noted that the sanitary condom case 10 essentially comprises a container 11 formed with a pivotally mounted lid 12 secured thereto by use of an elongate flexible hinge 13 formed generally parallel and securing respective rear faces of the respective container and lid. Securement of the container 11 and lid is effective by utilization of an elongate arcuate projection 14 integrally formed to an upper edge of a forward side of the container 11 for cooperation with an overlying elongate "L" shaped clip 15 defining a complementary recess cooperating with the arcuate projection 14.

The container 11 defines an interior wherein a resilient clip 17 is secured to an interior surface of a side wall of the container 11 and extends parallel to the forward and rear walls of the container 11 a distance less than the length of the container such that it is spaced from an opposed side wall to accommodate and secure a plurality of condoms "C" thereunder.

The lid 12 is formed with a top dispensing compartment 18 defining an interior formed onto the top surface of the lid 12 including an access opening 19 formed medially of the compartment 18 and generally parallel to opposed side walls of the lid 12. A flexible closure strip 20 is secured adjacent a rear edge of the lid 12 utilizing a securement hinge 21 formed generally parallel to the flexible hinge 13. The closure strip 20 defines a width greater than the width of the access opening 19. The closure strip 20 is formed with a continuous perimeter of first hook and loop fasteners 22 about a lowermost surface of the strip 20 to cooperate with companion second hook and loop fasteners 23 formed to an uppermost surface of the dispensing compartment 18. The second hook and loop fasteners are formed about the uppermost surface of the dispensing compartment 18 and about a forward wall of the lid 12 to completely enclose the access opening 19. A central sponge portion 24 is formed centrally and interiorly of the first hook and loop fasteners 22 and is of a width generally equal to that of the access opening 19 to overlie the access opening 19 to maintain moisture within the cleansing towels "T" positioned within the dispensing compartment 18.

An interior surface of the lid 12 includes a plurality of rigid clips 16 secured to and extending orthogonally interiorly of opposed side walls of the lid 12 to secure a sanitary dispensing bag "B" between the clips 16 and an interior surface of the lid 12, as illustrated in FIGS. 1 and 2 for example.

In this manner, the condoms "C" are readily available as are the cleansing towels "T" for cleansing purposes by an individual wherein the sanitary dispensing bag "B" enables secure disposal of the condom "C" and the towel "T", as the deemed necessary.

As to the manner of usage and operation of the instant invention, the same should be apparent from the above description and accordingly no further discussion relative to the manner of usage and operation of the instant invention shall be provided.

With respect to the above description then it is to be realized that the optimum dimensional relationship for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. A condom case comprising, in combination,
    a container defining a first cavity, and
    a lid defining a second cavity in overlying relationship to said first cavity and pivotally secured to and overlying said container, and
    fastening means for selectively securing said lid to said container, and
    first clip means integrally secured within said first cavity of said container for securing at least one condom therein, and
    second clip means integrally secured within said second cavity for securing a disposable bag therein, and
    further including a dispensing compartment integrally secured to a top portion of said lid wherein said dispensing compartment includes an access opening means for providing access to a plurality of moistened cleansing towels therein, and wherein said first clip means comprises a resilient elongate clip of a length less than a length defined by said container wherein said first clip is integrally secured to a side wall of said container and spaced from an opposing side wall of said container, and wherein said second clip means comprises a plurality of rigid clip members, each clip member is secured to an opposing side wall of said lid and spaced from an interior surface formed by the top of said lid.

2. A condom case as set forth in claim 1 wherein said access opening is formed medially of said dispensing compartment and generally parallel to the side walls of the lid.

3. A condom case as set forth in claim 2 further including a flexible closure strip selectively securable overlying said access opening wherein said closure strip is of a width greater than a width defined by said access opening.

4. A condom case as set forth in claim 3 wherein said flexible closure strip includes a continuus strip of first hook and loop fasteners cooperative with and of complementary configuration to a second strip of hook and loop fasteners formed about a perimeter of the access opening.

5. A condom case as set forth in claim 4 wherein said flexible strip further includes a central sponge portion formed within said first strip of hook and loop fasteners for maintaining moisture of said cleansing towels when said flexible strip is secured over said access opening.

6. A condom case as set forth in claim 5 wherein said fastening means includes an "L" shaped elongate downwardly depending clip integrally formed to a forward wall of said lid cooperating with an elongate arcuate projection integrally formed to a forward wall of said container wherein said arcuate projection is of a complementary configuration to a cavity defined by said "L" shaped when said "L" shaped clip is overlying said arcuate projection.

* * * * *